US009357928B2

United States Patent
Cheng

(10) Patent No.: US 9,357,928 B2
(45) Date of Patent: Jun. 7, 2016

(54) VIBRATIONAL PHOTOACOUSTIC TOMOGRAPHY USING RAMAN LASER

(71) Applicant: Purdue Research Foundation, West Lafayette, IN (US)

(72) Inventor: Ji-Xin Cheng, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 97 days.

(21) Appl. No.: 14/156,946

(22) Filed: Jan. 16, 2014

(65) Prior Publication Data

US 2014/0200434 A1    Jul. 17, 2014

Related U.S. Application Data

(63) Continuation-in-part of application No. PCT/US2013/023095, filed on Jan. 25, 2013.

(60) Provisional application No. 61/753,007, filed on Jan. 16, 2013, provisional application No. 61/872,414, filed on Aug. 30, 2013, provisional application No. 61/592,819, filed on Jan. 31, 2012.

(51) Int. Cl.
*A61B 5/05* (2006.01)
*A61B 5/00* (2006.01)

(52) U.S. Cl.
CPC .................... *A61B 5/0095* (2013.01)

(58) Field of Classification Search
USPC ......................................................... 600/407
See application file for complete search history.

(56) References Cited

U.S. PATENT DOCUMENTS

| 2001/0045529 | A1* | 11/2001 | Iketaki et al. ............... 250/493.1 |
| 2005/0154382 | A1* | 7/2005 | Altshuler et al. ................. 606/9 |
| 2005/0168735 | A1* | 8/2005 | Boppart et al. ............... 356/301 |
| 2010/0249570 | A1* | 9/2010 | Carson et al. ................. 600/407 |
| 2012/0271170 | A1 | 10/2012 | Emelianov et al. |
| 2013/0158383 | A1 | 6/2013 | Cheng et al. |

FOREIGN PATENT DOCUMENTS

| WO | WO0209246 A1 | 1/2002 |
| WO | WO2012024687 A2 | 2/2012 |

OTHER PUBLICATIONS

Wang et al (Label-free bond-selective imaging by listening to vibrationally excited molecules, Jun. 10, 2011).*

(Continued)

*Primary Examiner* — Joel F Brutus
(74) *Attorney, Agent, or Firm* — Purdue Research Foundation

(57) ABSTRACT

A method of noninvasively imaging tissue within a body includes irradiating the tissue using an imaging laser including a Raman-based laser tuner, the radiation including a plurality of laser pulses, each having energy greater than 100 mJ; receiving an acoustic signal generated by vibrational energy in the tissue, wherein the vibrational energy is a result of selective overtone excitation of molecules in the tissue by the radiation; and automatically converting the acoustic signal to an image representative of the tissue using a processor. An imaging system includes an imaging laser configured to irradiate tissue with a plurality of laser pulses using a Raman-based laser tuner. An ultrasonic transducer receives an acoustic signal generated by vibrational energy in the tissue due to overtone excitation by the radiation. A processor is configured to automatically produce an image representative of the tissue using the received acoustic signal.

15 Claims, 12 Drawing Sheets

(56) References Cited

OTHER PUBLICATIONS

Hartsuiker, L., "Microspectroscopic Characterisations of Gold Nanorods for Cancer Cell Detection", 2011, Ph. D. Dissertation, excerpt pp. 2, 6-172 DOI 10.3990/1.9789036532402; figure 1.6; p. 9, paragraph 2; p. 15, paragraphs 2-4; figure 2.2; p. 32, paragraph 1; figure 3.4; p. 38, paragraph 2; figure 3.5 (total 177 pages).

Tosi, MR et al., "Cholesteryl Esters in Malignancy", Clin. Chim. Acta. Sep. 2005. vol. 359, Nos. 1-2; pp. 27-45; abstract, (19 pages).

Yakovlev, W et al., Monitoring Stimulated Raman Scattering With Photoacoustic Detection. Opt Letter. Apr. 1, 2011, vol. 36, No. 7, pp. 133-1235, pp. 1-3; p. 2, paragraph 2; p. 3 paragraph 4 (3 pages).

Yue, S. et al., Multimodal Nonlinear Optical Microscopy, Laser & Photonics Reviews, Jul. 2011, vol. 5, No. 4, pp. 496-512; abstract. DOI: 10.1002/lpor.201000027, (17 pages).

Koljenovik, S., et al., Towards Clinico-Pathological Application of Raman Spectroscopy: Detection of Meningioma in Dura Mater by Raman Spectroscopy. Optima Grafische Communicatle, Rotterdam, The Netherlands. 2008, pp. 45-62. ISBN 978-90-8559-360-7 (originally published in: Analytical Chemistry. 2005, vol. 77, No. 24: 7958-7965); p. 53, paragraph 1; figure 2, (162 pages).

Hawi, Sr. et al Raman Microspectroscopy of Intracellular Cholesterol Crystals in Cultured Bovine Coronary Artery Endothelial Cells, Journal of Lipid Research. 1997, vol. 38, pp. 1591-1597; figure 2, (7 pages).

American Cancer Society, Testing Biopsy and Cytology Specimens for Cancer. Mar. 24, 2010, <URL: http://web.archive.org/web/20110226113555/http://www.cancer.org/treatment/understandingyougdiagnosis/examsandtestdescriptions/testingbiopsyandcytologysecimensforcancer/testing-biopsy-and-cytology-specimens-for-cancer-biopsy-types>; overview, (18 pages).

Remy, C et al., Evidence That Mobile Lipids Detected in Rat Brain Glioma by 1H Nuclear Magnetic REsonance Correspond to Lipid Droplets. Cancer Research. Feb. 1, 1997, vol. 57, pp. 407-414; p. 410, col. 1, paragraph 1; figure 4, (9 pages).

Guo, Y. et al., Lipid Droplets at AGlance, Journal of Cell Science, 2009, vol. 122, No. 6, pp. 749-752. DOI: 10.1242/jcs.037630; p. 749, col. 1, paragraph 1 to column, paragraph 1; p. 750, col. 2, paragraph 4 (4 pages).

ISA/US, International Search Report completed Jun. 12, 2013, from corresponding PCT Application No. PCT/US2013/023095 (5 pages).

ISA/US, Written Opinion of the ISA from corresponding PCT application No. PCT/SU2013/023095, as completed on May 17, 2013 (7 pgs.).

Hou, Yang et al., "Thin Polymer Etalon Arrays for High-Resolution Photoacoustic Imaging", 2008 Society of Photo-Optical Instrumentation Engineers, J. Biomed Opt. 2008; 13(6): 064033, doi: 10.1117/1.3042260, (20 pgs.).

Lee, Hung R. et al., "Birefringence Compensation in a Barium Nitrate Raman Laser", Copyright 1999, IEEE, CLEO, Pacific Rim '99/ ThG4, (2 pgs.).

Lux, Oliver et al., "Barium Nitrate Raman Laser for CO2 Detection", CLEO Technical Digest Copyright OSA 2012, Institute of Optics and Atomic Physics, Technical University of Berlin, Str. des 17, Juni, 10623 Berlin, Germany (2 pgs.).

Simons, Joshua et al., "Small-Scale, All-Solid-State, Frequency-Doubled Intracavity Raman Laser Producing 5 mW Yellow-Orange Output at 598 nm", Centre for Lasers and Applications, Macquarie University, North Ryde, NSW 2109, Australia, Optics Communications 229 (2004) 305-310, Copyright 2003 Elsevier, (6 pgs.).

Wang, Han-Wei et al, "Label-Free Bond-Selective Imaging by Listening to Vibrationally Excited Molecules", Copyright 2011 American Physical Society , 0031-9007/11/106)23 /238106(4), Physical Review Letters PRL 106, week ending Jun. 10, 2011, (4 pgs.).

Zverev, P. G. et al., "Barium Nitrate Raman Laser", Journal de Physique IV, General Physics Institute, Russian Academy of Sciences, Vavilov Str. 38, Moscow 117942, Russia, Article published online by EDP Sciences and available at http://dx.doi.org/10.1051/jp4:19944150 (2 pgs.).

Chen, Huiting et al., "High-Efficiency 1598.5-nm Third Stokes Raman Laser Based on Barium Nitrate Crystal", Copyright 2011, Chinese Optics Letters, Issue 07, vol. 04, 2006, 04(07): (1 pg.).

Chyba, Thomas et al., "Development of a Portable, Ground-Based Ozone Lidar Instrument for Tropospheric Ozone Research and Educational Training", NASA Research, Nasa Langley Research Center, Hampton, VA (US), Jul. 1, 1997-Jun. 30, 1999, Department of Physics Hampton University, Hampton, Virginia (27 pgs.).

Slypchenko, Mikhail N. et al., "Vibrational Imaging of Tablets by Epi-Detected Stimulated Raman Scattering Microscopy", RSC Publishing, Analys, 2010, DOI: 10.1039/C0an00252f, obtained from internet at http://www.rsc.org/delivery/_ArticleLinking/ArticleLinking.cfm?JournalCode=AN&Year=2010&manuscri . . . printed on Aug. 25, 2010 (10 pgs).

Zhang, Delong et al, "Highly Sensitive Vibrational Imaging by Femtosecond Pulse Stimulated Raman Loss", ACS Publications, The Journal of Physical Chemistry Letters Feb. 2011, 1248-1253, Copyright XXXX American Chemical Society (dx.doi.org/10.1021/jz200516n (6 pags.).

\* cited by examiner

VIBRATIONAL PHOTOACOUSTIC TOMOGRAPHY USING RAMAN LASER

CROSS-REFERENCE TO RELATED APPLICATIONS

This nonprovisional application claims the benefit of U.S. Provisional Application Ser. No. 61/753,007, filed Jan. 16, 2013 and of U.S. Provisional Application Ser. No. 61/872,414, filed Aug. 30, 2013 and is a continuation-in-part of International Application Ser. No. PCT/US2013/023095, filed Jan. 25, 2013 which claims the benefit of U.S. Provisional Application Ser. No. 61/753,007, filed Jan. 16, 2013 and of U.S. Provisional Application Ser. No. 61/592,819, filed Jan. 31, 2012 the entirety of each of which is incorporated herein by reference.

STATEMENT OF FEDERALLY SPONSORED RESEARCH OR DEVELOPMENT

This invention was made with Government support under Contract No. EB015901 awarded by the National Institutes of Health. The government has certain rights in the invention.

TECHNICAL FIELD

The present application relates to vibrational photoacoustic tomography, and more specifically to imaging tissue using vibrational photoacoustic tomography.

BACKGROUND

Spectroscopic signals from inherent molecular vibration offer a contrast mechanism for label-free imaging of biomolecules in cells and tissues. Accordingly, vibrational imaging of deep tissues holds great potential for in situ diagnosis based on the disrupted molecular mechanism in human diseases. However, vibrational imaging of deep tissues has been a formidable challenge due to tissue absorption and scattering of both incident photons and generated signals. For example, though coherent Raman scattering microscopy has allowed fast vibrational imaging, its penetration depth is limited to ~100 μm because the signal is generated by ballistic photons under a tight focusing condition.

As a molecular and functional imaging modality, photoacoustic tomography (PAT) has demonstrated the imaging capability of several centimeters deep into biological tissues. In PAT, pulsed light is used to induce optical absorption inside a tissue by diffused photons. Part of the absorbed energy is converted into heat, which raises the temperature of the absorbed region on the order of mK. This sudden temperature change then creates pressure transients and subsequent generation of photoacoustic (PA) waves detectable by an ultrasonic transducer in real time. From the measured signal, the distribution of optical absorbers is reconstructed. The contrast mechanism in PAT is generally based on electronic absorption in the near infrared region extending up to 950 nm. For example, PAT imaging of hemoglobin and exogenous contrast agents such as dyes and nanoparticles has been reported Inherent molecular vibration offers a contrast mechanism for chemical imaging in a label free manner. In vibrational microscopy based on either infrared absorption or Raman scattering, the imaging depth is limited to the ballistic photon mean free path, which is a few hundred microns in a biological sample. Owing to much weaker acoustic scattering in tissues as compared to optical scattering, photoacoustic detection of harmonic molecular vibration has enabled significant improvement in imaging depth. In this method, optical absorption is induced by overtone transitions at near infrared wavelengths, such as the second overtone transition of C—H bond occurring around 1200 nm. Upon excitation, this vibrational energy quickly turns into heat, which leads to bond-selective photoacoustic signals. Overtone transitions have been used for intravascular photoacoustic imaging of lipid accumulation. The optical parametric oscillator currently used for PAT has been designed for excitation of hemoglobin and other contrast agents in wavelengths below 950 nm.

However, effective vibrational photoacoustic tomography (VPAT) has not yet been demonstrated, partly due to the unavailability of a laser source having sufficient energy for diffused photon excitation of harmonic vibration. There is, therefore, a need of an improved laser and improved VPAT system.

BRIEF DESCRIPTION

According to an aspect, there is provided a method of noninvasively imaging tissue within a body, the method comprising:
   irradiating the tissue with radiation from an imaging laser including a Raman-based laser tuner, the radiation including a plurality of laser pulses from the laser to the tissue, each pulse having energy greater than 100 mJ;
   receiving an acoustic signal generated by vibrational energy in the tissue, wherein the vibrational energy is a result of selective overtone excitation of molecules in the tissue by the radiation; and
   automatically converting the acoustic signal to an image representative of the tissue using a processor.

According to another aspect, there is provided an imaging system comprising:
   a) an imaging laser including a Raman-based laser tuner and configured to irradiate tissue with a plurality of laser pulses, each pulse having energy greater than 100 mJ;
   b) an ultrasonic transducer configured to receive an acoustic signal generated by vibrational energy in the tissue, wherein the vibrational energy is a result of selective overtone excitation of molecules in the tissue by the radiation; and
   c) a processor configured to automatically produce an image representative of the tissue using the received acoustic signal.

Various embodiments advantageously provide improved contrast in VPAT imaging, higher pulse energy and correspondingly deeper tissue imaging, and excitation at wavelengths exhibiting natural resonances.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

Figure 1:
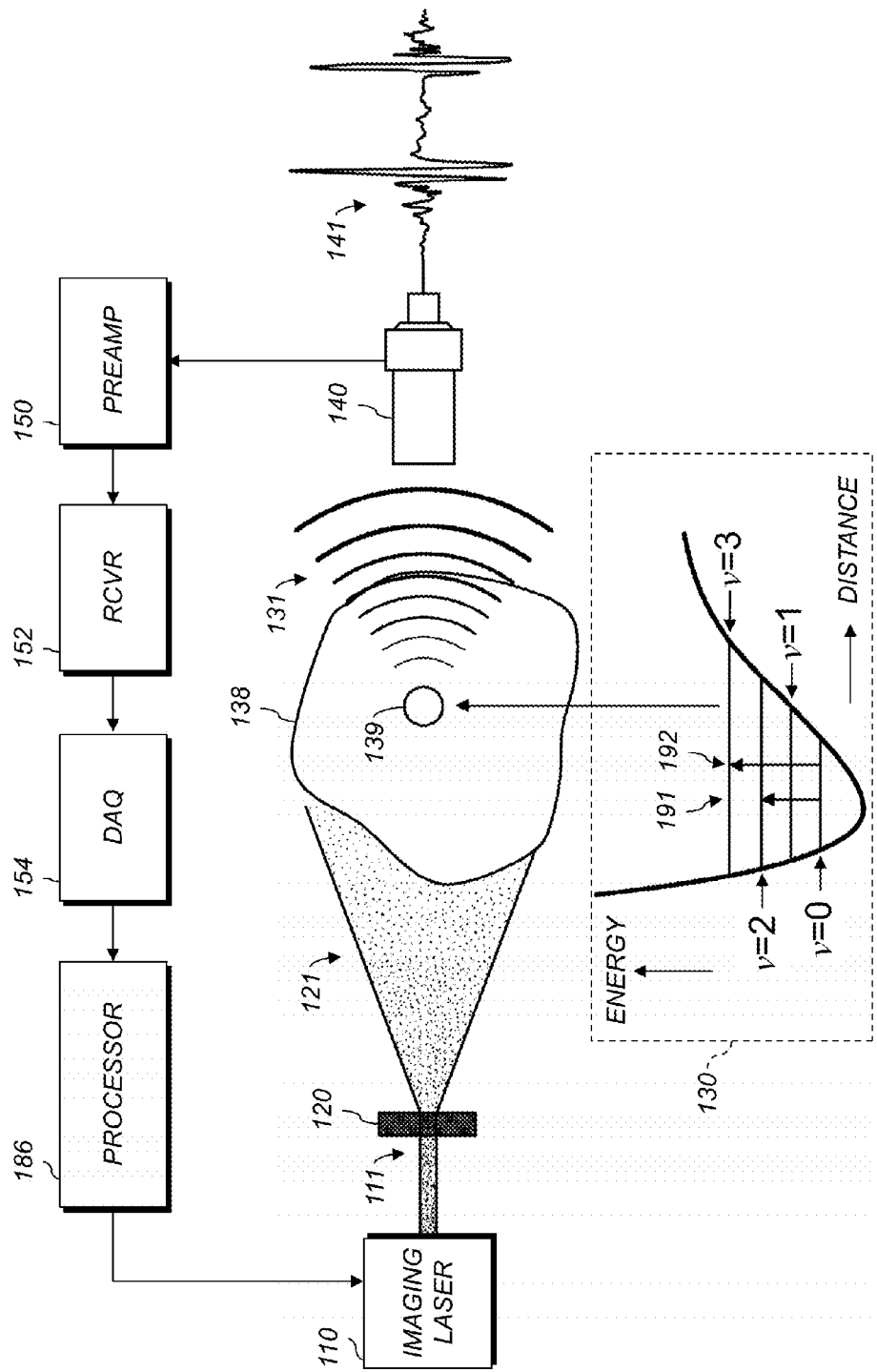
FIG. 1 depicts an exemplary vibration-based photoacoustic tomography (VPAT) system and illustrates the $1^{st}$ (2v) and $2^{nd}$ (3v) overtone absorption of an exemplary molecule.

The attached drawings are for purposes of illustration and are not necessarily to scale.

DETAILED DESCRIPTION

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Various exemplary devices and systems herein are based on vibrational photoacoustic microscopy, where a weakly focused near infrared nanosecond laser is used to induce an overtone transition in a specimen, and a focused transducer is employed to detect the acoustic signal in the forward direction.

In conventional schemes using focused radiation, the photoacoustic signal is produced by the focused photons. Thus, the imaging speed is limited by slow lateral scanning. In contrast, PA signals in various aspects herein are produced by diffused photons, where the imaging speed is significantly increased by ultrasonic array detection and the imaging depth is determined by tissue absorption which has a mean absorption length of 1.0 to 10 cm in the near infrared region. In various aspects, a laser in the VPAT device is a Raman laser that converts the 1064 nm pulses of a Nd:YAG laser to pulses at 1197 nm with a 36% conversion efficiency. The VPAT device is able to reach an imaging depth of ~5 cm and 3-D spatial resolution on the order of ~100 μm.

The device operates based on overtone excitation of molecular vibration targeting specific chemical bonds along with acoustic detection of pressure waves that are generated in a biological tissue as a result of the overtone excitation. The apparatus provides label-free (unstained and untagged) non-invasive or minimally invasive imaging that does not damage tissues during characterization of biomarkers within lipid droplets. Typically, a pulsed, wavelength-tunable, monochromatic radiation is directed into a sample. The wavelength of the radiation is adjusted to match the overtone vibrational frequency of a molecule at near-infrared region. Vibrational absorption of the incident radiation and subsequent conversion of the vibrational energy into heat generates a pressure transient inside a sample, thereby producing a detectable acoustic signal having molecule-specific information. As noted above, unlike microscopy, in VPAT, the entire object (or a sizeable portion thereof) is irradiated by the laser. Both the scattered and non-scattered photons contribute to the overtone absorption and subsequent generation of PA waves. Since the imaging depth is primarily determined by how deep the light can reach in a given sample, pulse energy of tens of mJ or more can be used for an object of few cubic cm in size.

Herein is described a platform that permits vibrational imaging of biological tissues beyond the ballistic regime. This platform, termed as vibration-based photoacoustic tomography (VP AT), is based on diffused photon excitation of harmonic vibration of chemical bond (i.e., overtone transitions from v=0 to 2, 3 . . . ) in the near infrared region, inherent relaxation of vibrational energy into heat, and acoustic detection of the generated ultrasound waves from the object. A barium nitrate $(Ba(NO_3)_2)$-crystal-based Raman laser with maximum output energy of 21.4 mJ per pulse was used for microscopic photoacoustic imaging of lipids in an experiment.

FIG. 1 depicts an exemplary vibration-based photoacoustic tomography (VPAT) system and illustrates the $1^{st}$ (2v) and $2^{nd}$ (3v) overtone absorption of an exemplary molecule 139 in a sample of tissue 138.

The VPAT imaging system includes imaging laser 110. Imaging laser 110 includes a Raman-based laser tuner, discussed below, and is configured to irradiate tissue with a plurality of laser pulses. Each pulse can have energy, e.g., greater than 100 mJ, or greater than 80 mJ, or greater than 60 mJ, or greater than 50 mJ. Radiation 111 from imaging laser 110 passes through optical diffuser 120 to provide diffused radiation 121 that strikes tissue 138. Diffuser 120 can be arranged on a beamline of the radiation 111 and between imaging laser 110 and tissue 138. Tissue 138 includes molecule 139 that absorbs some of the incident radiation 121.

A photoacoustic effect takes place when radiation is absorbed by molecule 139. The absorbed energy is converted to heat ($\Delta T \approx 10^{-3}$ K), which then causes local thermal expansion through the thermal elastic process. The thermal expansion thereafter generates a pressure wave transient that propagates through tissue 138 as acoustic signal 131. Ultrasonic transducer 140 is configured to receive acoustic signal 131 generated by vibrational energy in the tissue 138. Ultrasonic transducer 140 produces an electrical signal 141 (analog or digital) representative of the acoustic signal 131.

Figure 2:
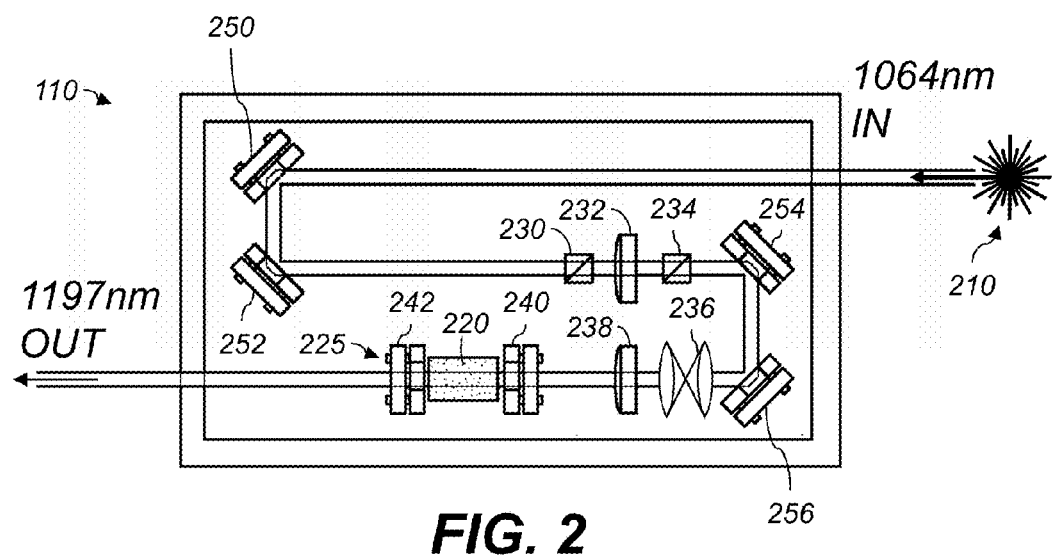
FIG. 2 shows a schematic of an exemplary imaging laser and related components.

Information obtained from the amplitude and the time-of-flight of the acoustic waves can be used to construct an image of the absorbing structure of tissues. Different biological tissues have different photoacoustic responses because of differences in absorption coefficient, thermal elasticity, size of absorber, etc. It should also be appreciated that different acoustic waves initiated by different structures arrive at the transducers at different times. This is because of flight times of these waves differ based on the depths of the structures, as the ultrasound waves propagate at the speed of sound within a tissue. According to one embodiment, a tunable nanosecond (ns) laser (e.g., FIG. 2) is used to induce overtone vibration absorption of selected molecules and more particularly, molecules with selected chemical bonds. The generated ultrasound waves (acoustic signal 131) are detected by transducer 140 and recorded through amplifier(s) and data acquisition devices. In the example shown, and in an experimental configuration that was tested, transducer 140 was an unfocused 10-MHz, 2-mm diameter ultrasonic transducer (XMS 310 by OLYMPUS NDT). Electrical signal 141 from transducer 140 was connected to a 20 dB preamplifier 150 followed by a receiver 152 (in the tested configuration, a 5072PR pulser/receiver by PANAMETRICS NDT, now OLYMPUS NDT with gain of 20 dB was used). The received signal was sent into a data acquisition (DAQ) unit 154 (as tested, a DAQ card), which was triggered by the Q-switch of Nd:YAG pump laser 210 (FIG. 2). The output from the DAQ was provided to processor 186.

Processor 186 is configured to automatically produce an image representative of the tissue using the received acoustic signal 131 (or the electrical signal 141 representative thereof, and likewise throughout). Further details of processor 186 are described below with reference to FIGS. 3 and 11. In various aspects, processor 186 can execute LABVIEW programs or other computer program instructions to control the pump laser 210 (FIG. 2) or imaging laser 110 to generate radiation pulses, to receive data from the ultrasound transducer 140 via the DAQ 154, and to process or display the received data.

The vibrational energy of acoustic signal 131 is a result of selective overtone excitation of molecule 139 in the tissue 138 by the radiation 121. As is well known in the art, the atoms in a molecule can vibrate, and each mode of vibration corresponds to one of a set of quantized energy levels. Vibrational absorption takes place when the incident photon frequency in radiation 121 matches a transition frequency between the vibrational states (v). In this situation, the photon can be absorbed and the vibrational state can change correspondingly.

Diagram 130 shows a representation of overtone excitation of molecule 139. In diagram 130, energy increases from bottom to top and inter-atomic distance increases from left to right. The $n^{th}$ overtone absorption takes place by transition from v=0 to v=n, with n $\in$ [2, 3, . . . ]. For example, second-overtone transition 191 is from v=0 to v=2, and third-overtone transition 192 is from v=0 to v=3.

In various aspects using near-infrared spectroscopic approaches, molecular spectra in chemical and biological samples can be excited according to radiation signals representing the overall overtone absorption and the elastic scattering in a sample. The spectral information can also be retrieved to perform a molecular scan or chemogram of biological tissues, e.g., to locate biomarkers such as cholesteryl ester within lipid droplets. Many of the second-overtone frequencies of molecules of interest are located in the near-infrared region from 700 to 1300 nm, where typical background tissue, e.g., of a human body, is minimally absorbing. Techniques described herein can be used to detect characteristic bands for a cholesterol ring at 428 $cm^{-1}$, 538 $cm^{-1}$, 614 $cm^{-1}$, and 702 $cm^{-1}$, an ester bond at 1742 $cm^{-1}$, a $CH_2$ deformation at 1448 $cm^{-1}$, a cholesterol-specific C—H stretch vibration at 2860 $cm^{-1}$, and the second overtone of C—H vibration around 1200 nm.

In various aspects, components shown in FIG. 1 are configured in the form of a catheter or other hollow body. Radiation 111, 121 is transmitted through the hollow body. Imaging laser 110 can be housed within the hollow body or outside of the hollow body and conveyed, e.g., via an optical fiber extending along the interior of the hollow body. Diffuse radiation 121 is directed onto a tissue and the transducer 140 is coupled to the hollow body such that it can detect a spectroscopic signal generated from tissue that has been excited by the imaging laser 110. For example, radiation 111 can be turned 90° by a lens and prism before diffuser 120. Radiation 121 and is directed through an optically transparent portion of, e.g., a subject's body so that radiation 121 impinges on tissue. The 90° direction is only exemplary and the radiation 111 can be redirected at any desired angle. Transducer 140 can be arranged to detect PA signals at, e.g., 90° off the long axis of the hollow body, or an angle corresponding to the angle of radiation 111.

In various aspects, components shown in FIG. 1 are configured in the form of an imaging probe, e.g., to be placed against the skin. Two arrays of optical fibers carry light from imaging laser 110 and can be arranged on either side of transducer 140. An array of transducers 140 can be arranged between the arrays of optical fibers. The optical fibers and transducer 140 can look straight ahead, such that the light from the imaging laser 110 is not redirected prior to exiting the optical fibers. Such a configuration permits forward-looking imaging. In certain embodiments, each fiber is slightly bent at the endpoints to facilitate the illumination of object towards the plane facing the center of the transducer array. A curved array transducer (C9-5ec, Philips Healthcare) with radius of curvature of 8 mm, a field of view of 150° and a frequency range of 5 to 9 MHz may be used to acquire the signals from the tissue. For each position of the probe or other device or system described herein, two images may be acquired sequentially at 1197 nm and 1064 nm. The two images can be compared to remove the non-vibration contrast. The data can be acquired in real time and the image reconstructed outside the system.

FIG. 2 shows a schematic of an exemplary imaging laser 110. Pump laser 210 is configured to supply energy to the imaging laser. The laser tuner in imaging laser 110 includes a $Ba(NO_3)_2$ crystal 220 arranged within a cavity 225 of imaging laser 110. Other types of crystals can be used as crystal 220, e.g., potassium gadolinium tungstate ($KGd(WO_4)_2$), $KYb(WO_4)_2$, $KY(WO_4)_2$, $CaCO_3$, $NaNO_3$, or $LiIO_3$. Crystal 220 can have a size of, e.g., 8 mm×8 mm×80 mm. This size of crystal permits providing large pulse energies, as described herein. Pump laser 210 can be configured to provide radiation having a wavelength substantially equal to 1064 nm, or other wavelengths. Imaging laser 110 can be configured to provide radiation having a wavelength substantially equal to 1197 nm, or substantially equal to 1200 nm, or other wavelengths. Examples of wavelengths and wavenumbers for various biomarkers of interest are given above. Compared to some prior systems, the Raman laser can be considerably less expensive. Moreover, crystal 220 can be arranged within the cavity of pump laser 210 (e.g., the Nd:YAG laser), rather than being provided after the cavity. Other types of crystals can be used besides $Ba(NO_3)_2$ Imaging laser 110 can be a solid-state Raman laser (also referred to as a "Raman shifter"). Stimulated Raman scattering in a gain medium provides wavelength shifts. The output wavelength of a Raman laser is determined by the pump wavelength (e.g., from pump laser 210) and the characteristic Raman shifts of the medium. For example, $Ba(NO_3)_2$ crystal 220 is an isotropic material with cubic symmetry. Its Raman spectrum is dominated by a strong peak at 1047 $cm^{-1}$, which corresponds to the "breathing" mode of the $NO_3$ molecular group. At room temperature, the Raman gain coefficient of the $Ba(NO_3)_2$ crystal 220 is 11 cm/GW, pumped by 1064 nm Nd:YAG pump laser 210. The optical damage threshold is ca. 400 MW/cm. An experiment was performed using a $Ba(NO_3)_2$ crystal-based Raman laser for vibration-based photoacoustic imaging. The Ba(NO3)$_2$ crystal was pumped by a Q-switched Nd:YAG pump laser 210 (CONTINUUM SURELITE SL III-10) operated with a 10 Hz repetition rate and 5 ns pulse duration (FWHM). Up to 21.4 mJ pulse energy at 1197 nm was obtained, corresponding to a conversion efficiency of 34.8%. Photoacoustic imaging of intramuscular fat sample was performed to demonstrate using a Raman laser to map lipid distribution in biological tissues, as is discussed below.

In the experiment, imaging laser 110 included polarizing beam splitter (PBS) 230 to purify the polarization of the fundamental 1064 nm laser light. A half-wave plate (HWP) 232 and a second PBS 234 were combined and used as a variable attenuator to adjust the pump pulse energy to obtain the desired output. In various aspects including that tested, telescope 236 including two positive lenses was employed to reduce the pump beam size to match the dimensions of the $Ba(NO_3)_2$ crystal 220. Other suitable optics can be used in place of telescope 236 depending on the size of crystal 220. After telescope 236, the beam in the experimental laser entered cavity 225 through quarter wave plate 238, which protected the Nd:YAG pump laser 210 from perturbation by backscattered light. For the experimental Raman laser, a flat-flat resonator with a cavity 225 having a length of about 10 cm was used. The resonator end mirror 240 was coated with high reflectivity at 1197 nm (R>99%) and high transmission at 1064 nm. The output coupler 242 was coated with high reflectivity at 1064 nm (R>99%) and 40% transmission at 1197 nm. The $Ba(NO_3)_2$ crystal 220, with dimensions of 4 mm×4 mm×38 mm, was coated with high transmission at 1064 nm and 1197 nm on both faces. Mirrors 250, 252, 254, 256 were 45° 1064 nm reflective mirrors. An additional silver mirror (not shown) can be placed following output coupler 242 to direct the output beam from imaging laser 110. For example, the silver mirror can be set at a 45° angle to turn the beam 90°.

Figure 3:
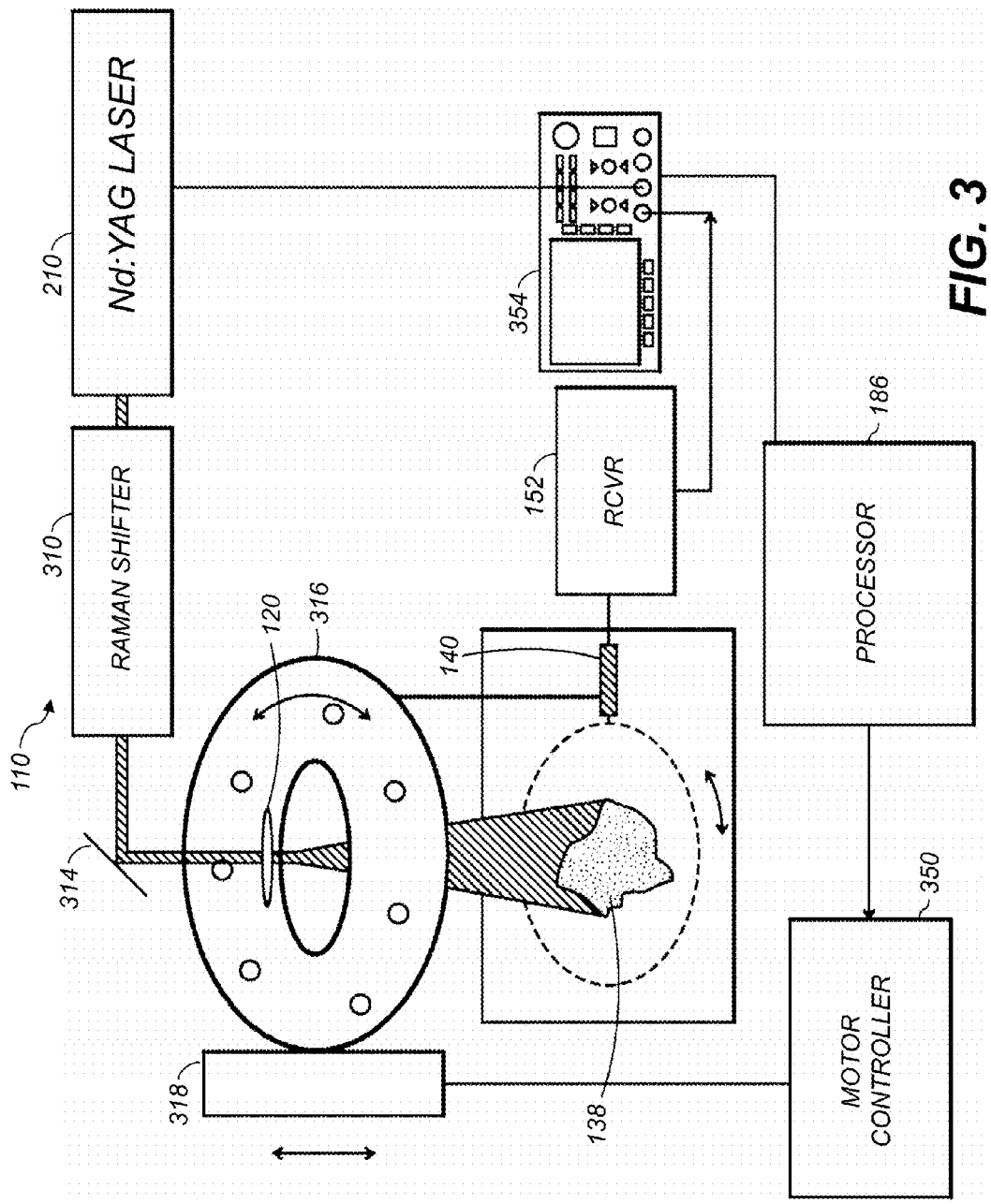
FIG. 3 is a schematic of a single-transducer VPAT imaging system.

FIG. 3 shows a schematic of an exemplary VPAT imaging system with a single element transducer 140. In an example, imaging laser 110 is a Raman laser including pump laser 210 as an energy source and Raman shifter 310. Raman shifter 310 can include a crystal 220 and other components described above with reference to FIG. 2. Imaging laser 110 provides the excitation source for the 1st C—H overtone transition. Mirror 314 can be used to direct the light from imaging laser 110. The light illuminates the tissue 138 after passing through a central hole of a rotational stage 316 in which a single element transducer 140 facing the tissue 138 is attached. The tissue 138 is placed inside a water proof gelatin gel. To provide acoustic coupling, both the transducer 140 and the tissue 138 are placed in a water bath. The transducer 140 is rotated by stage 316 in a circular path on a plane passing through the tissue 138. In various aspects, stage 316 is configured to change a position around an axis of the ultrasonic transducer 140 with respect to the tissue 138. The axis can be the main axis of diffuser 120, and imaging laser 110 can be arranged to irradiate the tissue 138 substantially along the axis, e.g., within 0±5° or 0±10° of the axis. The transducer 140 records the photoacoustic signal resulting from the irradiation, and the output of transducer 140 is amplified by receiver 152. The amplified signal is then fed into a channel of a digital oscilloscope 354, e.g., by TEKTRONIX, triggered by the pump laser 210. For each laser firing, the photoacoustic signal is acquired by the oscilloscope 354 and transferred to processor 186. After the acquisition of the first data, the transducer 140 is rotated by 2° and the next data is acquired. This is repeated until the 360° angle is covered. Other angles than 2° can be used.

Processor 186 can use the data acquired in one complete revolution to construct 2-D images, e.g., using back projection. In order to obtain 3-D images, the rotational stage 316 is coupled to translational stage 318. For each position of the transducer 140 along the axis above and below the plane passing through the center of the tissue 138, the circular scan is performed. Then processor 186 determines 3-D images by layer-by-layer stacking of the 2-D images. Specifically, in various aspects, processor 186 is configured to control imaging laser 110 and the stage(s) 316, 318 (e.g., via motor controller 350) to collect a plurality of acoustic signals using the ultrasonic transducer 140, each acoustic signal corresponding to a respective position around the axis described above (e.g., through diffuser 120). Processor 186 is further configured to produce the image by back-projecting the respective acoustic signals according to the respective positions around the axis.

An experiment was performed. An unfocused ultrasonic transducer 140 was used, as described above. The rotational stage 316 was moved in steps around the sample of tissue 138 in a circular path of radius 4.5 cm and the photoacoustic signal was acquired for each step until one complete revolution had been performed. A LabVIEW program was used to control the rotational stage and collect the data.

Various exemplary configurations include a laser comprising a barium nitrate $(Ba(NO_3)_2)$ amplifier, wherein the laser is configured to output a signal at 1197 nm. Input light can be received from a Nd:YAG laser. The input light can be at 1064 nm. The laser can include a beam splitter, e.g., a polarizing beam splitter. The laser can include a variable attenuator, e.g., including a half-wave plate and a polarizing beam splitter. The laser end mirror can be coated with high reflectivity at 1197 nm. The laser can include an output coupler mirror. The output coupler mirror can be coated with high reflectivity at 1064 nm and 40% transmission at 1197 nm. The barium nitrate can be in the form of a crystal, and the crystal can be coated with high transmission at 1064 nm and 1197 nm on both faces. An exemplary imaging system includes a laser, a tuner (e.g., a Raman tuner) coupled to the laser and configured to selectively generate an optical output having a predetermined wavelength, a diffuser, a transducer, and an imaging arrangement coupled to the transducer.

Figure 4A:
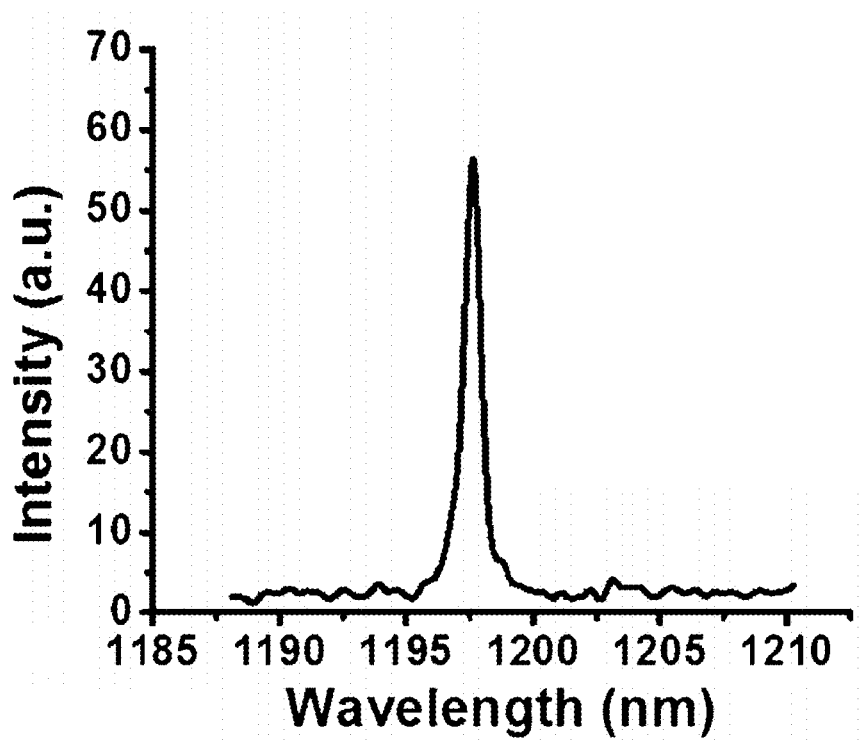
FIGS. 4A-4D show experimental data of a tested $Ba(NO_3)_2$-crystal-based Raman laser.
Figure 4B:
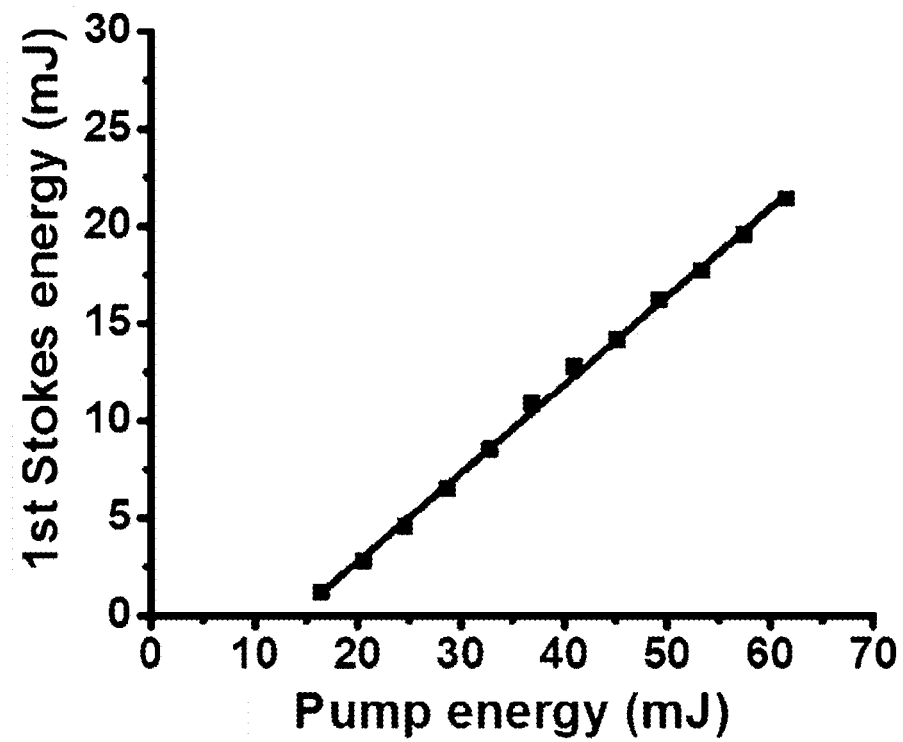
Figure 4C:
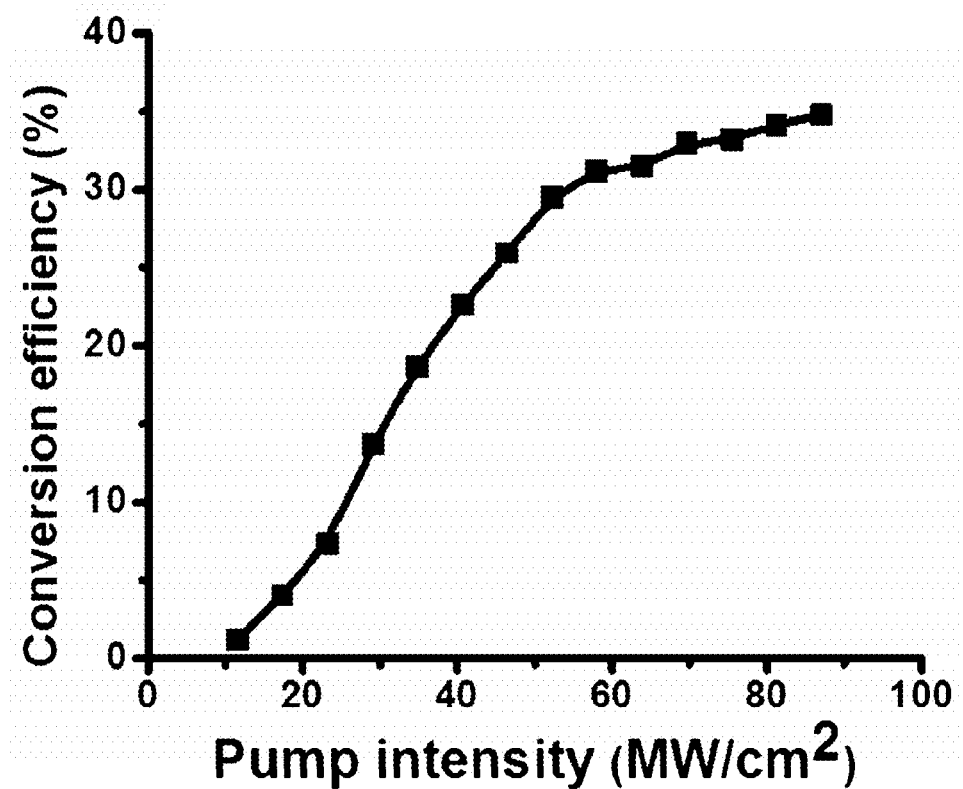
Figure 4D:
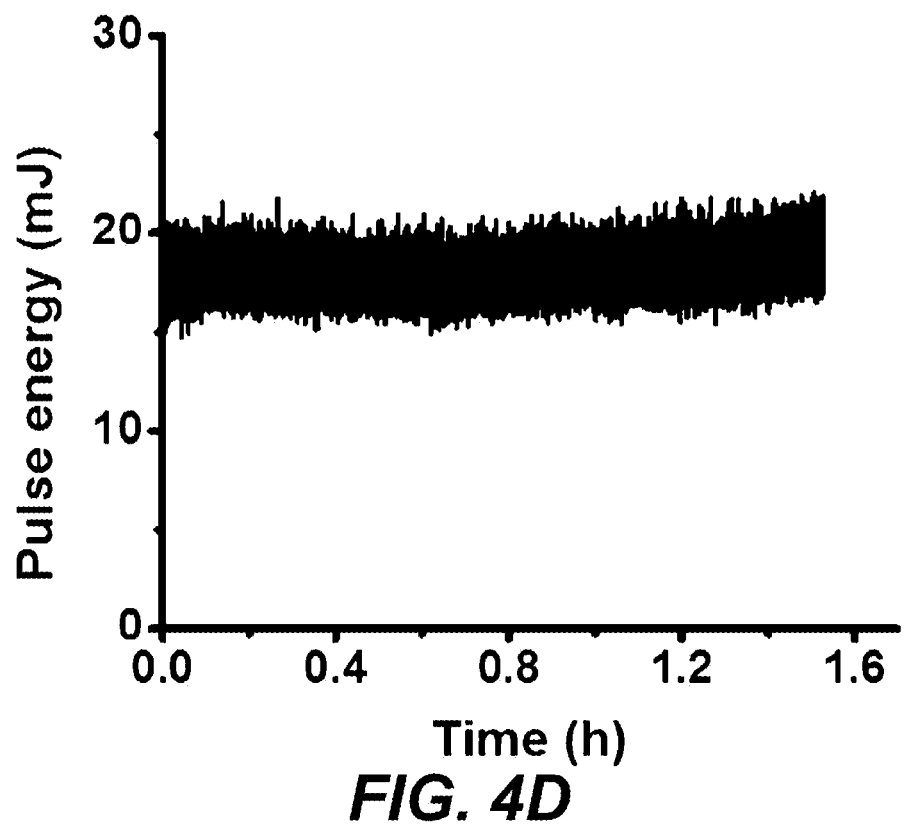

FIGS. 4A-4D show characteristics of a tested $Ba(NO_3)_2$-crystal-based Raman laser. FIG. 4A shows the spectral profile of the Raman laser output. FIG. 4B shows the $1^{st}$ Stokes energy as a function of the pump energy incident on the Raman crystal, and a linear fit thereof (solid line). FIG. 4C shows conversion efficiency with respect to the pump intensity incident on the Raman crystal 220 (FIG. 2). FIG. 4D shows pulse energy of Raman laser as a function of time.

In this test, 1197 nm light was produced by a Raman laser as described above with reference to FIG. 2, including telescope 236 and using a 4 mm×4 mm×38 mm crystal 220. The 1197 nm light was directed into an inverted microscope (1X71, Olympus) for photoacoustic imaging. An achromatic doublet lens (30 mm focal length, Thorlabs) was applied to focus the Raman laser on the samples. The photoacoustic signals were detected by a focused ultrasonic transducer (V317, Olympus NDT), followed by a preamplifier (5682, Olympus NDT) and a pulse receiver (5073 PR-15-U, Olympus NDT). The collected photoacoustic signals were then sent to a digitizer (USB-5133, National Instrument), and retrieved via a LabVIEW program running on processor 186. To perform 3D vibrational photoacoustic imaging, an XY translational stage 318 (ProScan HI 17, Prior) was employed for raster scanning of samples of tissue 138.

Referring to FIG. 4A, the spectral profile of the Raman laser output, measured by a USB 2000 spectrometer (Ocean Optics), indicates the central wavelength of ~1197.6 nm. In this experiment, he maximum pump energy was limited to 60 mJ by the crystal damage threshold, with maximum output pulse energy measured to be 21.4 mJ, corresponding to a slope efficiency of 45.4% (FIG. 4B). The conversion efficiency was computed as the pulse energy of the Raman laser divided by the pulse energy of the pump laser incident on the $Ba(NO_3)_2$ crystal. As shown in FIG. 4C, the maximum conversion efficiency is about 34.8%. This compares to 0.5% efficiency for a prior system using an optical parametric oscillator (OPO, the Panther EX Plus by Continuum). The threshold for the $1^{st}$ Stokes Raman laser was measured to be 11.6 MW/cm. FIG. 4D shows variation over a 1.5 hour period of the $1^{st}$ Stokes output energy obtained with 60 mJ pump energy (incident on the crystal 220). The maximum pulse energy drop was 12%, at least some of which may result from fluctuation of the Nd:YAG pump laser (6%).

Figure 5A:
FIGS. 5A-5E show experimental data of photoacoustic imaging of intramuscular fat performed with a tested Raman laser.
Figure 5B:
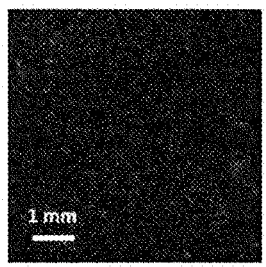
Figure 5C:
Figure 5D:
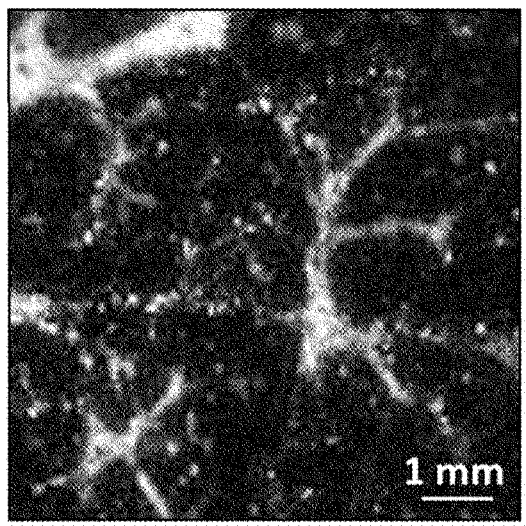
Figure 5E:

FIGS. 5A-E show experimental data of photoacoustic imaging of intramuscular fat performed with a tested Raman laser. FIG. 5A shows an en-face maximum intensity projection photoacoustic image of an intramuscular fat sample with 1197 nm excitation. FIG. 5B shows an en-face maximum intensity projection photoacoustic image of the intramuscular fat sample with 1064 nm excitation. FIG. 5C shows a histological evaluation of the same intramuscular fat sample. FIGS. 5D and 5E show a three-dimensional photoacoustic image of a separate intramuscular fat sample. A pulse energy of 60 μJ was used. The image size is 120×120 pixels.

Intramuscular fat was employed to demonstrate the capability of the Raman Laser for photoacoustic imaging. The muscle samples, which were cut into ~10 mm×10 mm×4 mm pieces, were harvested from a goat and then preserved in fixative 10% buffered formalin. A small muscle piece was then placed in a glass bottom dish and embedded with $H_2O$-agarose gel for the subsequent photoacoustic imaging. With the pulse energy of 60 μJ on the sample, photoacoustic imaging of intramuscular fat was conducted. FIG. 5A shows an on-resonant photoacoustic image and FIG. 5B shows an off-resonant photoacoustic image. A strong signal was found at 1197 nm (FIG. 5A) and the contrast nearly disappeared at 1064 nm (FIG. 5B). These data demonstrate that photoacoustic signal is generated from the C—H bond overtone vibration of lipid. This lipid imaging capability was further confirmed by histological examination of the same tissue (FIG. 5C), where the same morphology of fat (white color) was observed. On the same setup, 3D photoacoustic imaging of intramuscular fat (FIGS. 5D-5E), was performed with an axial resolution of 110 μm, a lateral resolution of 60 μm and an imaging depth of ~3 mm.

Experimental data described herein show photoacoustic imaging of lipids with a compact $Ba(NO_3)_2$ crystal-based Raman laser. Up to 21.4 mJ pulse energy at 1197 nm was produced, corresponding to the conversion efficiency of 34.8%. The high conversion efficiency of the Raman laser permits vibrational photoacoustic tomography by using a larger $Ba(NO_3)_2$ crystal to endure larger incident pulse energy and generate 100 mJ pulse energy at 1197 nm. In various aspects, energy levels can be selected based on standards such as American National Standard Z136.1-2000. Photoacoustic tomography with overtone vibration as contrast permits bond-selective imaging of biological tissues with an imaging depth and field of view both on the centimeter scale.

Figure 6:
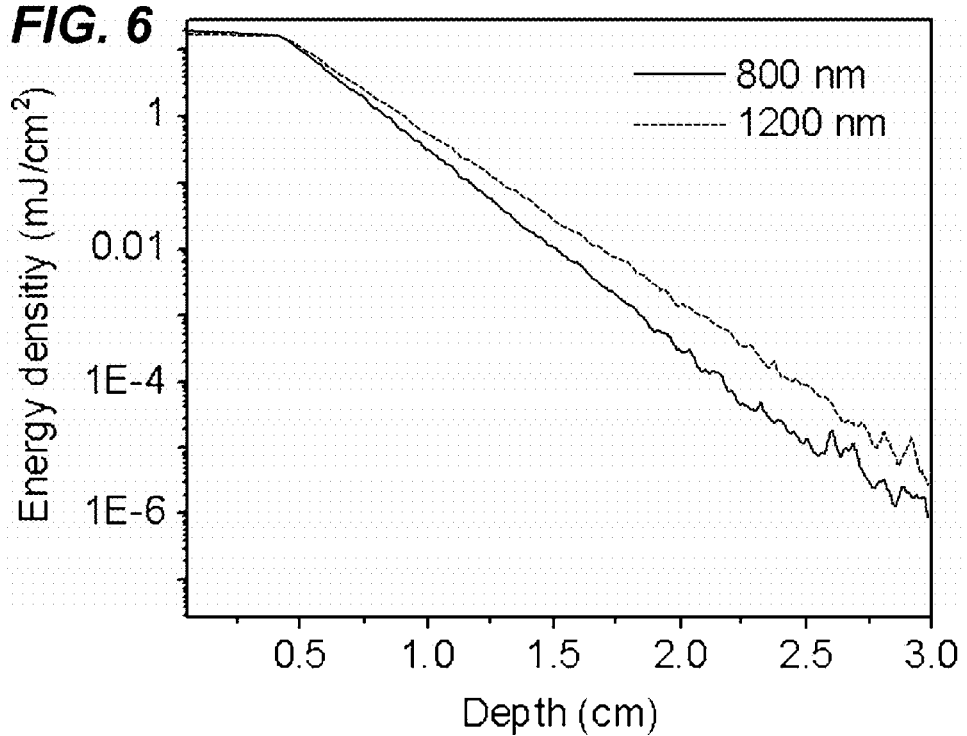
FIG. 6 is a graph showing a Monte Carlo simulation of energy density versus depth.

FIG. 6 is a graph showing a Monte Carlo simulation of energy density (fluence) versus depth at two wavelengths of incident radiation: 800 nm (solid) and 1200 nm (hatched). The simulation was performed to evaluate the effect of scattering and absorption on VPAT imaging depth. The photon energy density in deep tissue at 1200 nm was estimated by Monte Carlo simulations and compared to that at 800 nm, where PAT imaging of blood is often performed. For the simulation, a tissue with two layers was used. The layers are a dermis of thickness 0.4 cm ($\mu_a$=0.11 cm$^{-1}$, $\mu_s'$=2.18 cm$^{-1}$ at 800 nm; $\mu_a$=0.13 cm$^{-1}$, $\mu_s'$=1.65 cm$^{-1}$ at 1200 nm) and subcutaneous tissue ($\mu_a$=1.07 cm$^{-1}$, $\mu_s'$=11.6 cm$^{-1}$ at 800 nm; $\mu_a$=1.06 cm$^{-1}$, $\mu_s'$=7.91 cm$^{-1}$ at 1200 nm) of varying thickness from 0 to 2.6 cm. Tissue optical parameters such as absorption and scattering coefficients were obtained from Tuchin (Tuchin, V. *Tissue Optics: Light Scattering Methods and Instruments for Medical Diagnosis*. SPIE Press, Bellingham, Wash., USA: 2007) and a refractive index of 1.4 was used. The simulated energy density versus the depth is given in FIG. 6. For example, at 3.0 cm depth, the light fluence is reduced by ~8 orders of magnitude, suggesting the need for high energy laser to perform VPAT. Moreover, it is noted that the fluence for 1200 nm at 2.0 cm depth is 5 times higher than that for 800 nm. Such enhancement is due to lower scattering coefficients at longer wavelengths. Since the PA signal is proportional to light fluence, this result indicates that 1200 nm excitation is beneficial for deep tissue vibrational imaging.

Figure 7:
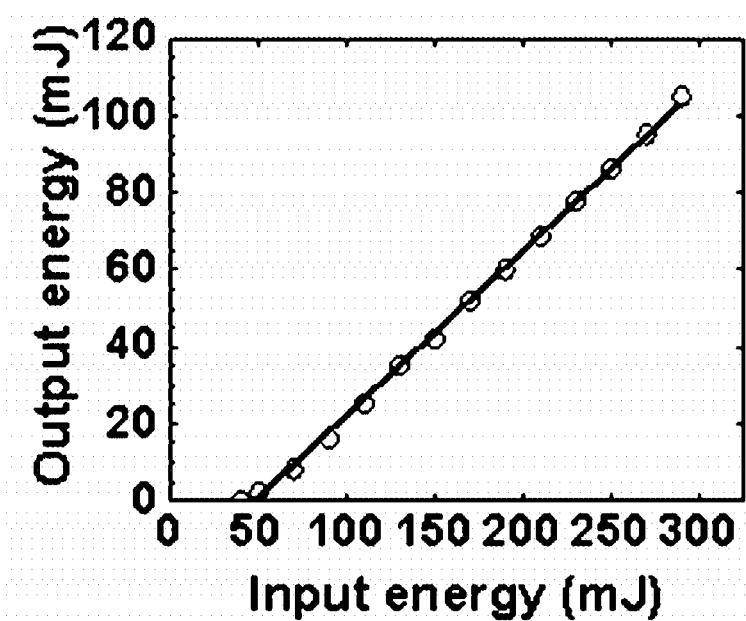
FIG. 7 shows experimental data of a tested laser configuration.

FIG. 7 shows experimental data of another tested configuration. Performance of the laser was tested by measuring the output energy versus the input energy. Also, the energy was monitored as a function of time to examine the long term stability. FIG. 7 shows the output versus the input energy. The output energy varies linearly with the input in the range from 50 to 290 mJ. With the input energy of 290 mJ, an output of 105 mJ was obtained at 1197 nm, corresponding to a conversion efficiency of 36%. Such efficiency is higher than conventional optical parametric oscillator technology by ~100 times at the specified wavelength. The Raman laser showed high stability over a time period of 1.5 hr (see, e.g., FIG. 4D). This stability advantageously permits acquiring high quality tomography images.

An experiment was performed using a Raman laser generating greater than 100 mJ of energy per pulse at 1197 nm wavelength to excite second-overtone transitions of C—H bonds. Vibrational photoacoustic signals from a C—H-rich polyethylene tube phantom placed under 3 cm thick chicken breast tissue were obtained with a signal to noise ratio of 2.5. A photoacoustic image of a polyethylene ring placed under 5 mm chicken tissue was recorded with effective contrast. The tested aspect and other aspects herein permit performing label free vibrational imaging in the deep tissue regime.

Figure 8A:
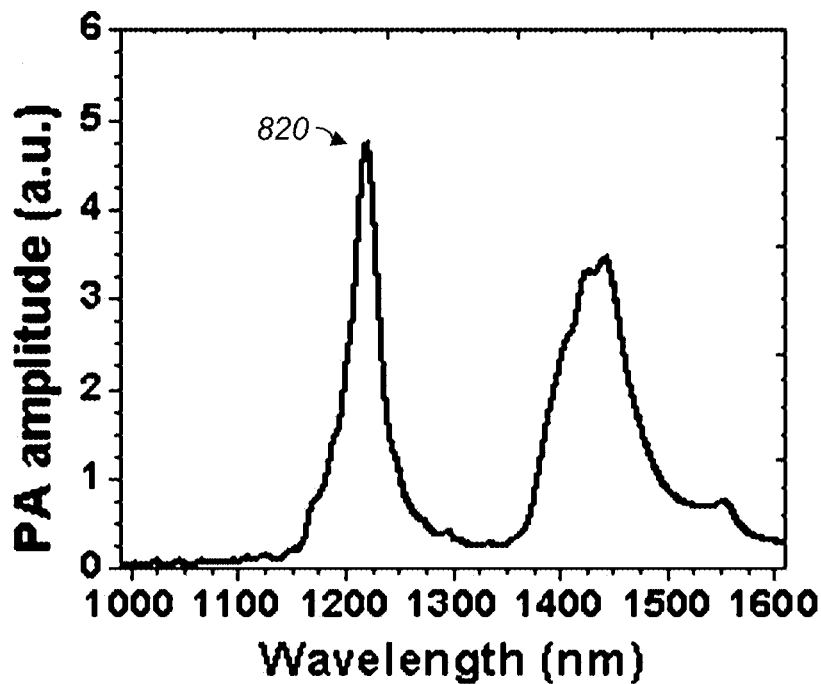
FIGS. 8A-8D show experimental data of a tested system imaging a polyethylene phantom.

FIG. 8A shows a photoacoustic spectrum of a polyethylene phantom. Polyethylene includes C—H bonds that have a second-overtone transition at peak 820. In the spectral window shown here, there are two signal bands, one peaked at ~1200 nm and the other peaked at ~1440 nm. The first band centered at 1200 nm (peak 820) corresponds to the second overtone absorption of C—H bond stretching vibration. The wavelength of the Raman laser used in this study is within this absorption band. In an experiment, a phantom made of a polyethylene tube was used. The tube had an outer diameter of 1.0 mm and an inner diameter of 0.6 mm.

Figure 8B:
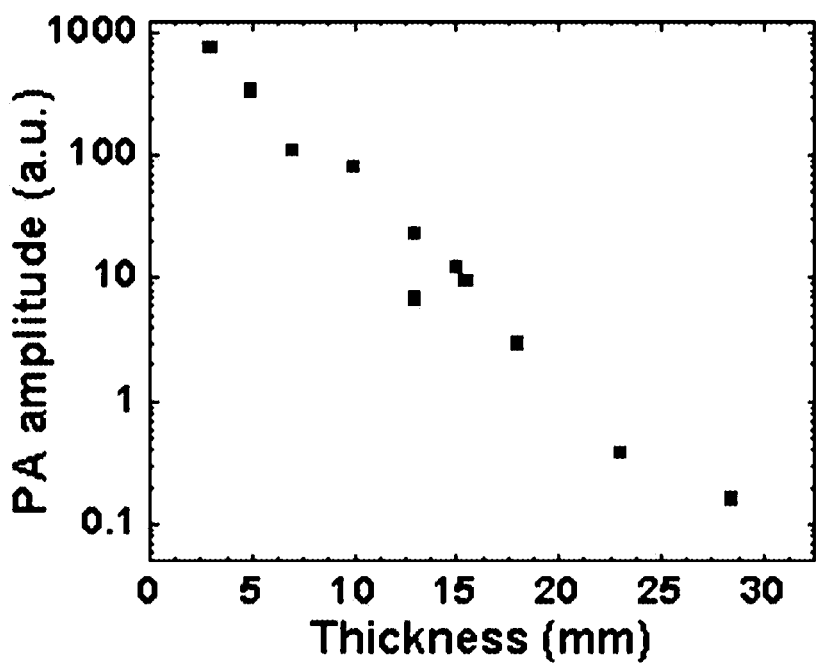

FIG. 8B shows experimental data of one-dimensional PA measurements on a 3 mm long polyethylene tube sample. A fresh chicken breast tissue layer was placed above the sample to simulate the in vivo situation. Laser energy of 57 mJ/cm$^2$ was sent to the sample through the chicken tissue layer (FIG. 4). The layer thickness was varied and the corresponding PA signal from the sample was measured. Then, the peak to peak amplitude of the PA signal was estimated.

FIG. 8B shows the peak-to-peak signal amplitude as a function of the thickness of the chicken-breast layer. FIG. 8B shows a variation of more than three orders of magnitude in PA amplitude over 3 cm thickness range. The pattern of the plot follows a linear relationship in log scale (in accordance with Beer's law relating light transmission and path length).

Figure 8C:
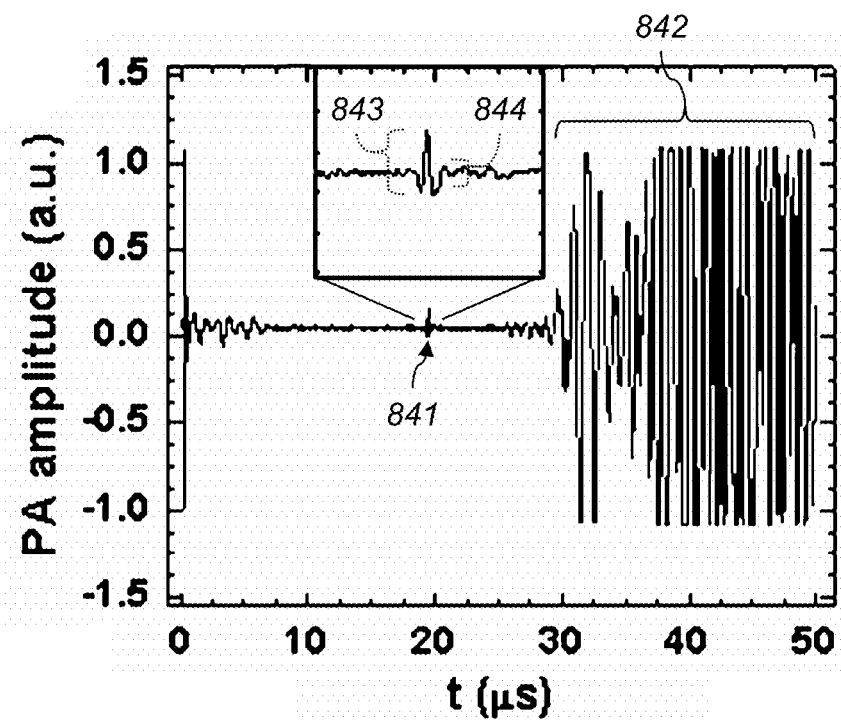

FIG. 8C shows an exemplary acoustic signal captured with a chicken-breast thickness of 3 cm. Signal 841 is a signal from the polyethylene target (the inset shows a magnified view). Signal 842 is a signal from chicken breast. PA signal 842 is present because part of the incident radiation was absorbed by the chicken tissue. In this experiment, the chicken tissue was placed at a distance from the polyethylene tube to permit separating the two PA signals 841, 842 based on the time delay. To obtain this data at 3 cm thickness, an average of 100 pulse excitations was performed and a group of 20 data sets were taken and then averaged. For other depths, due to higher signal to noise ratio, averages of smaller number of pulses were carried out. As shown, the signal to noise ratio of signal 841 was 2.5 at 3 cm thickness. The inset shows signal range 843, which is 2.5 times as tall as noise range 844.

Figure 8D:
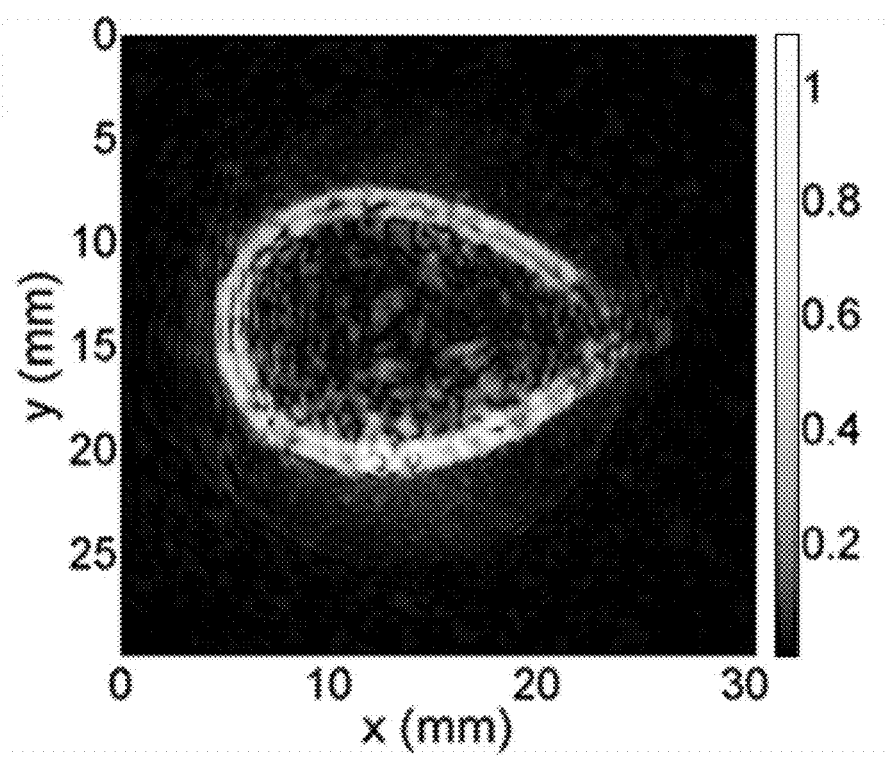

FIG. 8D shows an experimental VPAT image and the corresponding value scale. In the experiment, two dimensional VPAT imaging was performed with a phantom made out of the same polyethylene tube. Two ends of a piece of the tube were joined together by using an epoxy to form a ring shape. The ring was then placed approximately at the center of the circular path of the transducer 140 by gluing it on a glass tube with epoxy. A 5 mm thick chicken breast layer was placed at a distance of 5 mm above the ring. Pulses from the Raman laser set at 80 mJ with a beam diameter of 1.0 cm irradiated the chicken tissue and illuminated the ring. The transducer 140 was rotated in steps of 2° and the PA signal was collected for each step at a rate of 100 kHz, until a complete revolution. Ten pulses were averaged for each measurement. It took about 10 minutes for acquisition of a complete set of data. The image was then reconstructed using a modified back projection algorithm. An image of the polyethylene ring obtained from the VPAT system is shown in FIG. 8D. The image showed effective contrast with no significant background contributed by water at the wavelength of 1197 nm.

A further experiment was performed. According to the ANSI safety standards, the maximum permissible exposure on skin in the near IR wavelength region is 100 mJ/cm$^2$. Various tested Raman laser configurations conform to that standard. Other configurations can be designed to conform to other standards. An experiment was performed to investigate effects of the incident radiation on cells in the tissues. A standard cell-viability test was performed using six-well plates containing cultured human prostate cancer PC3 cells. Three wells were irradiated for 30 sec by 1197 nm laser pulses with 100 mJ/cm$^2$ energy density, and three wells were controls. Immediately after irradiation, cells were stained by calcein and propidium iodide for 15 min and then imaged on a confocal microscope. The numbers of damaged cells and of viable cells were counted, based on the staining by propidium iodide and calcein respectively, and no significant cell death was found. Various aspects therefore permit deep-tissue imaging in vivo.

Figure 9:
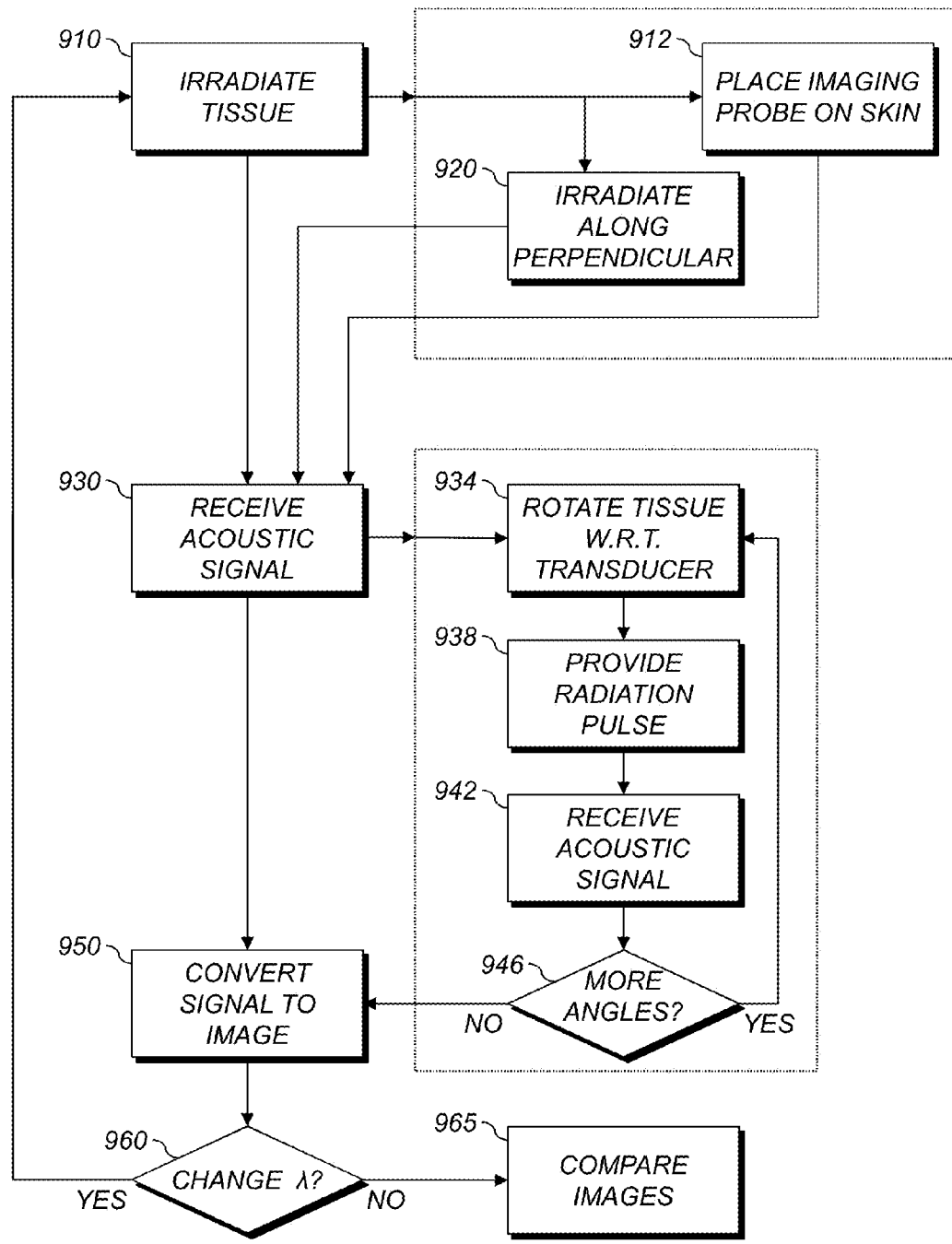
FIG. 9 shows a flowchart illustrating an exemplary method for noninvasively imaging tissue within a body.

FIG. 9 shows a flowchart illustrating an exemplary method for noninvasively imaging tissue within a body. The steps can be performed in any order except when otherwise specified, or when data from an earlier step is used in a later step. In at least one example, processing begins with step 910. For clarity of explanation, reference is herein made to various components shown in FIGS. 1-3 that can carry out or participate in the steps of the exemplary method. It should be noted, however, that other components can be used; that is, exemplary method(s) shown in FIG. 9 are not limited to being carried out by the identified components.

In step 910, the tissue 138 is irradiated with radiation from an imaging laser 110 including a Raman-based laser tuner 310. The radiation includes a plurality of laser pulses from the laser to the tissue 138, each pulse having energy greater than 100 mJ. This can be done as described above, e.g., with reference to FIG. 1, 2, or 3. Step 910 can include step 912 or step 920, and can be followed by step 930.

In various exemplary aspects, step 910 can includes passing energy through the laser tuner, the laser tuner having a Ba(NO$_3$)$_2$ crystal arranged within a cavity of the laser as discussed above with reference to FIG. 2. Step 910 can also or alternatively include providing energy to the cavity of the laser using a pump laser 210, e.g., an Nd:YAG laser. The pump laser 210 can have an output wavelength substantially equal to 1064 nm (e.g., 1064±5 nm, or ±10 nm, or ±20 nm), the imaging laser 110 can have an output wavelength substantially equal to 1197 nm (e.g., 1197±5 nm, or ±10 nm, or ±20 nm), and the tissue 138 can include atoms having C—H bonds, so that the radiation from the imaging laser 110 excites the second overtone vibrational band of the C—H bonds.

In step 912, an imaging probe is placed on skin of the body over the tissue 138. The imaging probe is configured to irradiate the tissue. The tissue can include an artery, e.g., a carotid artery. The tissue can include, e.g., epithelial tissue.

In step 920, the radiation is applied to the tissue 138 along a direction substantially perpendicular to a direction between the tissue 138 and the ultrasonic transducer 140. This step can be used, e.g., with a configuration including a rotational stage 316 such as the configuration shown in FIG. 3. The direction can be, e.g., at an angle between 75° and 105° with the direction between the tissue 138 and the ultrasonic transducer 140.

In step 930, an acoustic signal is received. The acoustic signal is generated by vibrational energy in the tissue, e.g., as described above with reference to FIG. 3. The vibrational energy is a result of selective overtone excitation of molecules in the tissue by the radiation, e.g., as discussed above with reference to diagram 130 (FIG. 1). Step 930 can be followed by step 950, and can include steps 934, 938, 942, 946.

In step 934, tissue 138 is rotated with respect to (w.r.t.) the ultrasonic transducer, e.g., by moving the transducer around tissue 138 or by rotating tissue 138 in place. In step 938, a radiation pulse is provided. In step 942, an acoustic signal is received using an ultrasonic transducer. In decision step 946, if there are more rotational positions (e.g., angles) to measure, step 934 is next. In this way, a plurality of acoustic signals is received, each respective acoustic signal corresponding to a respective rotational position of the tissue 138 w.r.t. the ultrasonic transducer 140. When no angles remain to be measured, step 950 is next.

In step 950, the acoustic signal is automatically converted to an image representative of the tissue using processor 186. Step 950 can include back-projecting the respective acoustic signals according to the respective rotational positions, e.g., of rotational stage 316. In various aspects, decision step 960 is next.

Figure 11:
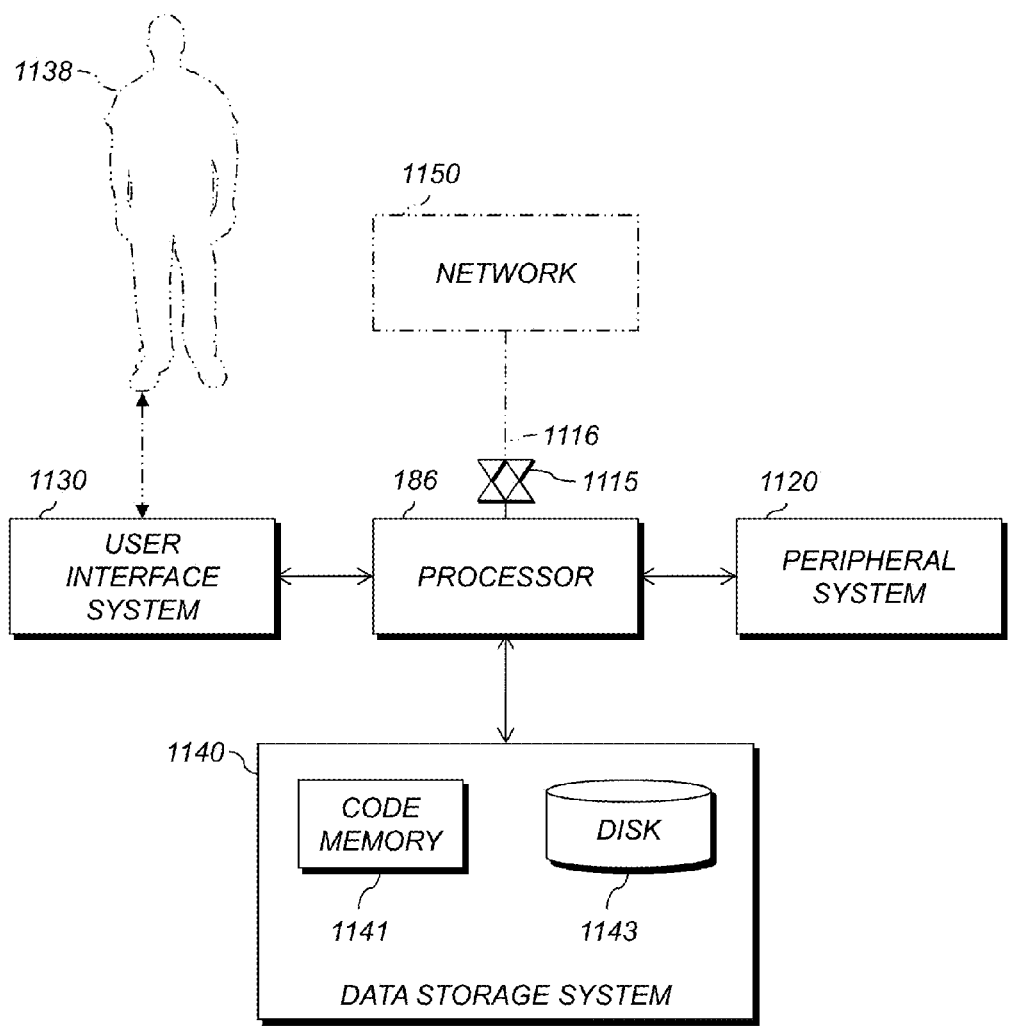
FIG. 11 is a high-level diagram showing components of a data-processing system.

In decision step 960, it is determined whether an image should be captured at a different wavelength. Processor 186 can determine this, e.g., by retrieving a stored user preference from data storage system 1140 (FIG. 11). If so, the next step is step 910. Steps 910, 930, and 950 are thus repeated at a different wavelength. For example, steps 910, 930, 950 can be performed for 1197 nm, and then performed again for 1064 nm. If no more images are to be captured, step 965 is next.

In step 965, the captured images at various wavelengths are compared to improve contrast. This can be done, e.g., by subtracting the off-resonance image from the on-resonance image.

In various embodiments of photoacoustic tomography, the transducer(s) 140 collect the photoacoustic signal from all regions on a spherical plane with radius determined by the time of flight and the speed of sound in the imaging medium. It is an inverse problem to obtain the chromophore information from the time resolved data. This computational task of reconstructing the image from the raw data can be time-consuming. The modified back-projection method is a useful image reconstruction method in photoacoustic tomography. Various aspects described herein use a modified back projection algorithm to speed up the image reconstruction process. Various aspects provide image reconstruction three times faster than conventional algorithms when applied to data from a 128-element transducer imaging system.

Figure 10:
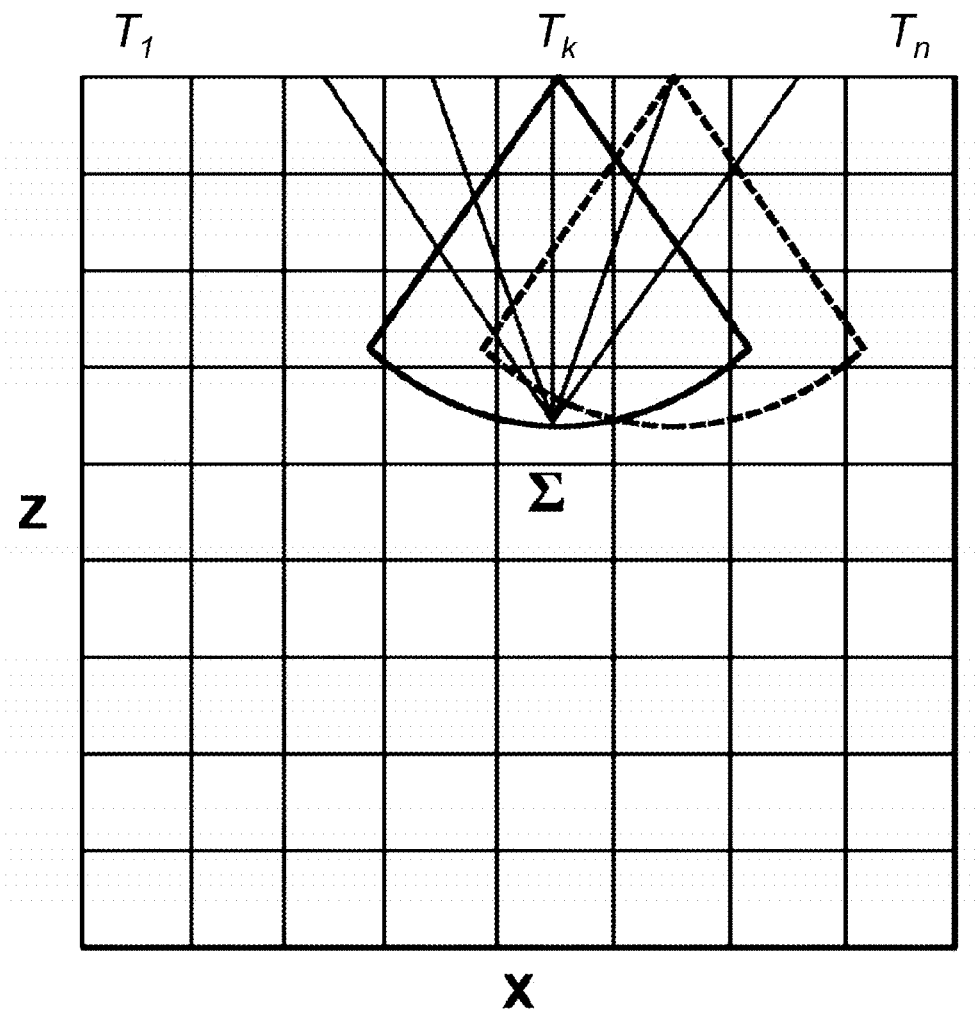
FIG. 10 shows an exemplary reconstruction matrix.

FIG. 10 shows an exemplary reconstruction matrix with each element corresponding to a pixel (FIG. 55). In the conventional method, first an angle is chosen such that each transducer ($T_1, \ldots, T_n$) element has a selected sensitivity within that angle. Alternatively, a pixel can only contribute to a set of transducers within that angle (straight lines). For each pixel ($\Sigma$), first the transducer group within the angle is identified, then the time of flight for each transducer is obtained by dividing the distance between the pixel and transducer by $v_s$, the speed of sound in the relevant medium. Then all the signals from the transducers are added coherently to obtain the final value for that pixel. Conventional versions of this procedure find the transducer set for each pixel individually and also determine the distance between each transducer and pixel separately.

In order to speed up the reconstruction procedure, various aspects approach the reconstruction problem in the opposite way conventional techniques do. Instead of going from pixel to transducer, an exemplary algorithm herein starts with the transducers and goes to each pixel. In this procedure, first a center element (e.g., $T_k$) is considered and starts with a given z (depth). Then, for a given angle, this transducer can contribute to pixels within the arc specified by the angle with radius of curvature equal to z (solid wedge shape). Next the pixels falling within the arc are determined and assigned the same transducer value ($T_k[t_i];=z/v_s$). Once these computations have been performed for one transducer ($T_k$) for a given z, then for other transducers the index is replaced, e.g., replace k by k+1 for the next transducer (shown as dotted-line wedge shape) or by k−1 for the previous transducer. The same procedure is repeated for all z. Because, for each z, only one calculation is needed, this algorithm can speed up the reconstruction procedure significantly compared to prior techniques.

Accordingly, various aspects described herein provide vibrational photoacoustic imaging, e.g., at high speeds. A technical effect is to irradiate a target (e.g., tissue 138) with light (including electromagnetic radiation both within and outside of the human visible range) from a Raman laser and determine the structure of the target by detecting acoustical signals resulting from light-increased energy of chemical bonds in the target. Various aspects include a larger $Ba(NO_3)$ crystal (also referred to herein as a laser tuner) than prior schemes and do not focus the input laser. Not focusing the input laser reduces the probability of photodamage to crystal 220 (FIG. 2) and still makes effective use of high pulse energy of the input, e.g., from pump laser 210. This permits a herein-described Raman laser to produce stable laser pulses at 1197 nm with pulse energy exceeding 100 mJ. Since this wavelength falls within the second overtone vibrational band of C—H bond, C—H rich species can be imaged in tomography mode. A further technical effect is to provide a visual representation of the tissue on a display screen. FIGS. 5A, 5B, and 8D show exemplary visual representations.

FIG. 11 is a high-level diagram showing the components of an exemplary data-processing system for analyzing data and performing other analyses described herein, and related components. The system includes a processor 186, a peripheral system 1120, a user interface system 1130, and a data storage system 1140. The peripheral system 1120, the user interface system 1130 and the data storage system 1140 are communicatively connected to the processor 186. Processor 186 can be communicatively connected to network 1150 (shown in phantom), e.g., the Internet or an X.115 network, as discussed below. DAQ 154, receiver 152, oscilloscope 354, and motor controller 350 can each include one or more of systems 186, 1120, 1130, 1140, and can each connect to one or more network(s) 1150. Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 186 can implement processes of various aspects described herein, e.g., with reference to FIGS. 9 and 10. Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 186 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1120, user interface system 1130, and data storage system 1140 are shown separately from the processor 186 but can be stored completely or partially within the processor 186.

The peripheral system 1120 can include one or more devices configured to provide digital content records to the processor 186. For example, the peripheral system 1120 can include digital still cameras, digital video cameras, cellular phones, or other data processors. The processor 186, upon receipt of digital content records from a device in the peripheral system 1120, can store such digital content records in the data storage system 1140.

The user interface system 1130 can include a mouse, a keyboard, another computer (connected, e.g., via a network or a null-modem cable), or any device or combination of devices from which data is input to the processor 186. The user interface system 1130 also can include a display device, a processor-accessible memory, or any device or combination of devices to which data is output by the processor 186. The user interface system 1130 and the data storage system 1140 can share a processor-accessible memory. Visual representations of VPAT images or data can be presented to user 1138 (shown in phantom) via user interface system 1130.

In various aspects, processor 186 includes or is connected to communication interface 1115 that is coupled via network link 1116 (shown in phantom) to network 1150. For example, communication interface 1115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1115 sends and receives electrical, electromagnetic or optical signals that carry digital or analog data streams representing various types of information across network link 1116 to network 1150. Network link 1116 can be connected to network 1150 via a switch, gateway, hub, router, or other networking device.

Processor 186 can send messages and receive data, including program code, through network 1150, network link 1116 and communication interface 1115. For example, a server can store requested code for an application program (e.g., a JAVA applet) on a tangible non-volatile computer-readable storage medium to which it is connected. The server can retrieve the code from the medium and transmit it through network 1150 to communication interface 1115. The received code can be executed by processor 186 as it is received, or stored in data storage system 1140 for later execution.

Data storage system 1140 can include or be communicatively connected with one or more processor-accessible memories configured to store information. The memories can be, e.g., within a chassis or as parts of a distributed system. The phrase "processor-accessible memory" is intended to include any data storage device to or from which processor 186 can transfer data (using appropriate components of peripheral system 1120), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1140 can be a tangible non-transitory computer-readable storage medium, i.e., a non-transitory device or article of manufacture that participates in storing instructions that can be provided to processor 186 for execution.

In an example, data storage system 1140 includes code memory 1141, e.g., a RAM, and disk 1143, e.g., a tangible computer-readable rotational storage device such as a hard drive. Computer program instructions are read into code memory 1141 from disk 1143. Processor 186 then executes one or more sequences of the computer program instructions loaded into code memory 1141, as a result performing process steps described herein. In this way, processor 186 carries out a computer implemented process. For example, steps of methods described herein, blocks of the flowchart illustrations or block diagrams herein, and combinations of those, can be implemented by computer program instructions. Code memory 1141 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 186 (and possibly also other processors), to cause functions, acts, or operational steps of various aspects herein to be performed by the processor 186 (or other processor). Computer program code for carrying out operations for various aspects described herein may be written in any combination of one or more programming language(s), and can be loaded from disk 1143 into code memory 1141 for execution. The program code may execute, e.g., entirely on processor 186, partly on processor 186 and partly on a remote computer connected to network 1150, or entirely on the remote computer.

The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

PARTS LIST 110 imaging laser
111 radiation
120 diffuser
121 radiation
130 diagram
131 acoustic signal
138 tissue
139 molecule
140 transducer
141 electrical signal
150 preamplifier
152 receiver
154 data acquisition (DAQ) unit
186 processor
191 second-overtone transition
192 third-overtone transition
210 pump laser
220 crystal
225 cavity
230 polarizing beamsplitter
232 half-wave plate
234 polarizing beamsplitter
236 telescope
238 quarter wave plate
240 resonator end mirror
242 output coupler 250, 252, 254, 256 mirrors
310 Raman-based laser tuner
314 mirror
316 rotational stage
318 translational stage
350 motor controller
354 oscilloscope
820 peak
841, 842 signals
843 signal range
844 noise range
910, 912, 920, 930 steps
934, 938, 942 steps
946 decision step
950 step
960 decision step
965 step
1064 fundamental
1115 communication interface
1116 network link
1120 peripheral system
1130 user interface system
1138 user
1140 data storage system
1141 code memory
1143 disk
1150 network
Σ pixel

The invention claimed is:

1. A method of noninvasively imaging tissue within a body, the method comprising:
irradiating the tissue with radiation from an imaging laser including a Raman-based laser tuner, radiation including a plurality of laser pulses from the imaging laser to the tissue, each pulse having energy greater than 100 mJ;
receiving an acoustic signal generated by vibrational energy in the tissue,
wherein the vibrational energy is a result of selective overtone excitation of molecules in the tissue by radiation; and
automatically converting the acoustic signal to an image representative of the tissue using a processor;
the irradiating step includes providing energy to a cavity of the imaging laser using Nd:YAG laser,
and the Nd:YAG laser has an output wavelength between 1044 nm 1084 nm, the imaging laser has an output wavelength between 1177 nm and 1217 nm, and the tissue includes atoms having C—B bonds, so that radiation from the imaging laser excites a second overtone vibration band of the C—H bonds.

2. The method according to claim 1, wherein the irradiating step includes passing energy through the laser tuner having a $Ba(NO_3)_2$ crystal arranged within a cavity of the imaging laser.

3. The method according to claim 2, wherein the irradiating step includes providing energy to the cavity of the imaging laser using a Nd:YAG laser.

4. The method according to claim 1, wherein the irradiating step includes placing an imaging probe on skin of the body over the tissue, wherein the imaging probe is configured to irradiate the tissue.

5. The method according to claim 1, wherein the receiving step includes rotating the tissue with respect to an ultrasonic transducer, providing a plurality of radiation pulses, and receiving respective acoustic signals using the ultrasonic transducer, each respective acoustic signal corresponding to a respective rotational position of the tissue with respect to the ultrasonic transducer.

6. The method according to claim 5, the irradiating step including applying radiation to the tissue along a direction substantially perpendicular to a direction between the tissue and the ultrasonic transducer.

7. The method according to claim 6, the converting step including back-projecting the respective acoustic signals according to the respective rotational positions.

8. An imaging system comprising:
a) an imaging laser including a Raman-based laser tuner and configured to irradiate tissue with a plurality of laser pulses, each pulse having energy greater than 100 mJ;
b) an ultrasonic transducer configured to receive an acoustic signal generated by vibrational energy in the tissue, wherein the vibrational energy is a result of selective overtone excitation of molecules in the tissue by radiation; and
c) a processor configured to automatically produce an image representative of the tissue using the received acoustic signal;
wherein using Nd:YAG laser to provide energy to a cavity of the imaging laser using Nd:YAG laser,
and the Nd:YAG laser has an output wavelength between 1044 nm 1084 nm, the imaging laser has an output wavelength between 1177 nm and 1217 nm, and the tissue includes atoms having C—B bonds, so that radiation from the imaging laser excites a second overtone vibration band of the C—H bonds.

9. The imaging system according to claim 8, the laser tuner including a $Ba(NO_3)_2$ crystal arranged within a cavity of the imaging laser.

10. The imaging system according to claim 9, further including a Nd:YAG laser configured to supply energy to the imaging laser.

11. The imaging system according to claim 9, wherein the crystal has a size of 8 mm×8 mm×80 mm.

12. The imaging system according to claim 8, further including a stage configured to change a position around an axis of the ultrasonic transducer with respect to the tissue.

13. The imaging system according to claim 12, wherein the imaging laser is arranged to irradiate the tissue substantially along the axis.

14. The imaging system according to claim 13, wherein the processor is configured to control the imaging laser and the stage to collect a plurality of acoustic signals using the ultrasonic transducer, each acoustic signal corresponding to a respective position around the axis, and the processor is further configured to produce the image by back-projecting the respective acoustic signals according to the respective positions around the axis.

15. The imaging system according to claim 8, further including a diffuser arranged on a beamline of radiation between the imaging laser and the tissue.

* * * * *